United States Patent
Honda

(10) Patent No.: US 7,803,108 B2
(45) Date of Patent: Sep. 28, 2010

(54) IN-VIVO IMAGE ACQUIRING APPARATUS, RECEIVING APPARATUS, AND IN-VIVO INFORMATION ACQUIRING SYSTEM

(75) Inventor: Takemitsu Honda, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 993 days.

(21) Appl. No.: 11/595,048

(22) Filed: Nov. 9, 2006

(65) Prior Publication Data

US 2007/0118017 A1 May 24, 2007

(30) Foreign Application Priority Data

Nov. 10, 2005 (JP) ............................. 2005-326615

(51) Int. Cl.
*A61B 1/04* (2006.01)
(52) U.S. Cl. ...................................... 600/118; 600/109
(58) Field of Classification Search .................. 600/101, 600/109, 117, 118, 160, 424, 476; 348/65, 348/68, 69, 74; 396/17
See application file for complete search history.

(56) References Cited

U.S. PATENT DOCUMENTS

| 6,951,536 | B2 * | 10/2005 | Yokoi et al. ................... 600/128 |
| 7,486,981 | B2 * | 2/2009 | Davidson ..................... 600/407 |
| 7,553,276 | B2 * | 6/2009 | Iddan .......................... 600/160 |
| 7,578,788 | B2 * | 8/2009 | Yokoi et al. ................... 600/160 |
| 2002/0109774 | A1 * | 8/2002 | Meron et al. ................... 348/74 |
| 2003/0023150 | A1 * | 1/2003 | Yokoi et al. ................... 600/300 |
| 2003/0117491 | A1 |  6/2003 | Avni et al. |
| 2003/0181788 | A1 * | 9/2003 | Yokoi et al. ................... 600/160 |
| 2004/0171914 | A1 * | 9/2004 | Avni ........................... 600/160 |
| 2004/0199061 | A1 |  10/2004 | Glukhovsky |
| 2005/0043583 | A1 * | 2/2005 | Killmann et al. ............. 600/160 |

(Continued)

FOREIGN PATENT DOCUMENTS

CN 1572228 A 2/2005

(Continued)

OTHER PUBLICATIONS

Office Action dated Aug. 21, 2009 received from the China Patent Office.

(Continued)

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

An object of the present invention is to enable a receiving side to easily recognize which of imaging devices has picked up received image data. A capsule endoscope (one example of the in-vivo image acquiring apparatus) of the present invention is swallowed by a subject, and picks up images of the inside of organs of the subject. The capsule endoscope has a plurality of LEDs, a plurality of CCDs, and a transmission module. The CCDs paired with the LEDs pick up images of the inside of a body cavity illuminated by the LEDs. The transmission module adds identification data for identifying the CCDs to image data in front and rear directions of the capsule endoscope picked up by the CCDS, and transmit the image data together with the identification data to the receiving side.

5 Claims, 9 Drawing Sheets

U.S. PATENT DOCUMENTS

| | | |
|---|---|---|
| 2005/0049462 A1 | 3/2005 | Kanazawa |
| 2005/0123179 A1* | 6/2005 | Chen et al. .................. 382/128 |
| 2006/0106318 A1* | 5/2006 | Davidson .................... 600/476 |

FOREIGN PATENT DOCUMENTS

| | | |
|---|---|---|
| DE | 103 23 216 B3 | 12/2004 |
| EP | 1 685 788 A1 | 8/2006 |
| JP | 2003-19111 | 1/2003 |
| JP | 2003-325439 | 11/2003 |
| JP | 2004-222937 | 8/2004 |
| JP | 2005-143991 | 6/2005 |
| JP | 2005143991 A * | 6/2005 |
| JP | 2005-305180 | 11/2005 |
| WO | WO 02/080376 A2 | 10/2002 |

OTHER PUBLICATIONS

Japanese Patent Abstract of Japan for Japanese Publication No. 2003-01911, published Jan. 21, 2003.

Japanese Patent Abstracts of Japan for Japanese Publication No. 2003-325439, published Nov. 18, 2003.

Japanese Patent Abstract of Japan for Japanese Publication No. 2004-222937, published Aug. 12, 2004.

* cited by examiner

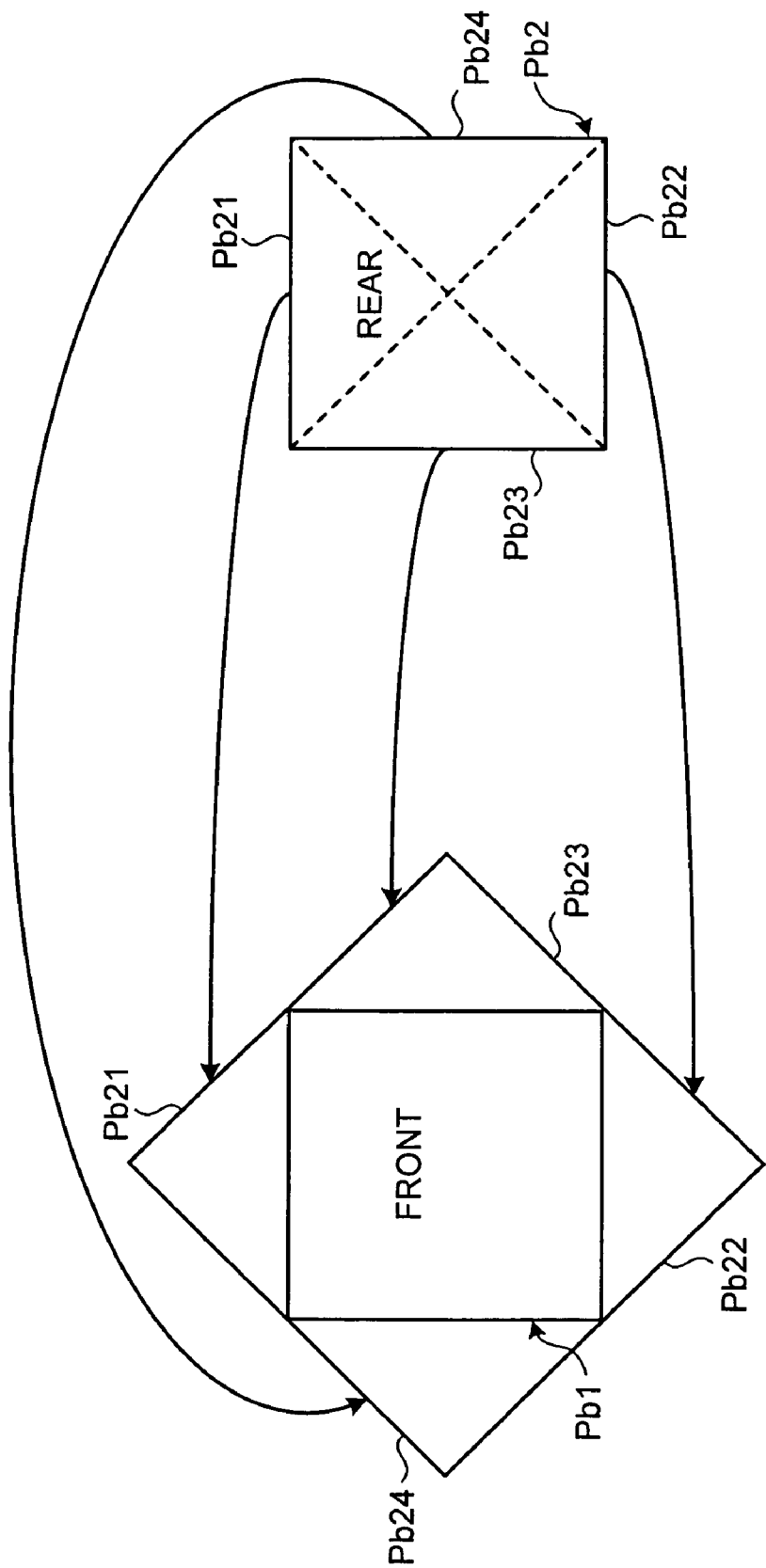

US 7,803,108 B2

IN-VIVO IMAGE ACQUIRING APPARATUS, RECEIVING APPARATUS, AND IN-VIVO INFORMATION ACQUIRING SYSTEM

CROSS-REFERENCE TO RELATED APPLICATIONS

The present application claims priority to Japanese Patent Application No. 2005-326615 filed on Nov. 10, 2005, the entire contents of which are hereby incorporated as reference.

BACKGROUND OF THE INVENTION

1. Field of the Invention

The present invention relates to an in-vivo image acquiring apparatus such as a pantoscopic capsule endoscope, a receiving apparatus that receives image data or the like from the in-vivo image acquiring apparatus, and an in-vivo information acquiring system using them.

2. Description of the Related Art

In recent years, capsule endoscopes which are provided with an imaging function and a radio communicating function have appeared in the field of endoscopes. After the capsule endoscope is swallowed by an examinee as a subject from the mouth for observation (examination) and until naturally discharged from a living body (human body) of the examinee, the capsule endoscope moves through insides of organs such as esophagus, stomach, and small intestine (the inside of a body cavity) according to their peristaltic motions, and sequentially picks up images at a predetermined imaging rate using the imaging function.

Image data, which are picked up in the body cavity by the capsule endoscope during the observation period in which the capsule endoscope is moving through the inside of the organs, are sequentially transmitted to the outside of the subject by the radio communicating function, and are accumulated in a memory provided in an external receiver. After the observation, doctors or nurses can make the images of the body cavity displayed on a display unit such as a display based on the image data accumulated in the memory of the receiver to make diagnosis (see Japanese Patent Application Laid-Open No. 2003-19111).

Generally, the capsule endoscopes as described above are monocular capsule endoscopes which only pick up images of body cavity located in its advancing direction, i.e., at its front side, but in recent years, a pantoscopic capsule endoscope which picks up images on the front and rear sides of the advancing direction is proposed in order to enlarge a visual field at the time of observing esophagus or the like (see U.S. patent application Laid-Open No. 2004/199061). In the pantoscopic capsule endoscope, a plurality of imaging blocks are provided to the front and rear sides of a capsule casing so as to pick up images on the front and rear sides of an advancing direction of the capsule casing in the body cavity. Each of the imaging blocks has a pair of an illuminating unit such as LED which illuminates the inside of a body cavity and an imaging device such as CCD which picks up an image of the inside of the illuminated body cavity.

However, U.S. patent application Laid-Open No. 2004/199061 merely describes that the pantoscopic capsule endoscope has the plurality of imaging devices that pick up images in the front and rear directions, and does not describe transmission control for transmitting the image data and display control at the time of displaying the images. As a result, the advantage of the pantoscopic capsule endoscope is not effectively utilized.

SUMMARY OF THE INVENTION

An in-vivo image acquiring apparatus according to one aspect of the present invention, includes: a first imager that serves to acquire image data; a second imager that serves to acquire image data which is formed independent of the image data acquired by the first imager; and a transmission data generator that generates transmission data by receiving the image data from the first and the second imagers and adding identification data, which allows for identification of the imager, to each piece of the image data.

A receiving apparatus according to another aspect of the present invention includes: a receiver that receives image data to which identification data is added; an identifying unit that identifies which imager picks up the image data received by the receiver based on the identification data added; and a storage unit that has divided storage areas and stores the image data in the storage areas according to the imagers identified by the identifying unit.

An in-vivo information acquiring system according to still another aspect of the present invention includes: an in-vivo image acquiring apparatus that includes a first imager that serves to acquire image data, a second imager that serves to acquire image data which is formed independent of the image data acquired by the first imager, a transmission data generator that generates transmission data by receiving the image data from the first and the second imagers and adding identification data, which allows for identification of the imager, to each piece of the image data, and a transmitter that performs radio transmission based on the transmission data generated by the transmission data generator; and a receiving apparatus that includes a receiver that receives data transmitted by the transmitter, an identifying unit that identifies which imager picks up the image data included in the data received by the receiver based on the identification data added, and a storage unit that has divided storage areas and stores the image data in the storage areas according to the imagers identified by the identifying unit.

The invention itself, together with further objects, features, and attendant advantages, will best be understood by reference to the following detailed description taken in conjunction with the accompanying drawings.

BRIEF DESCRIPTION OF THE DRAWINGS

FIG. 9 is a diagram of one example of an image displayed on the display screen of the display apparatus.

DETAILED DESCRIPTION OF THE PREFERRED EMBODIMENTS

Exemplary embodiments of an in-vivo image acquiring apparatus, a receiving apparatus, and an in-vivo information acquiring system of the present invention are explained in detail below with reference to FIGS. 1 to 9. The present invention is not limited to these embodiments, and can be variously changed without departing from the gist of the present invention.

First Embodiment

Figure 1:
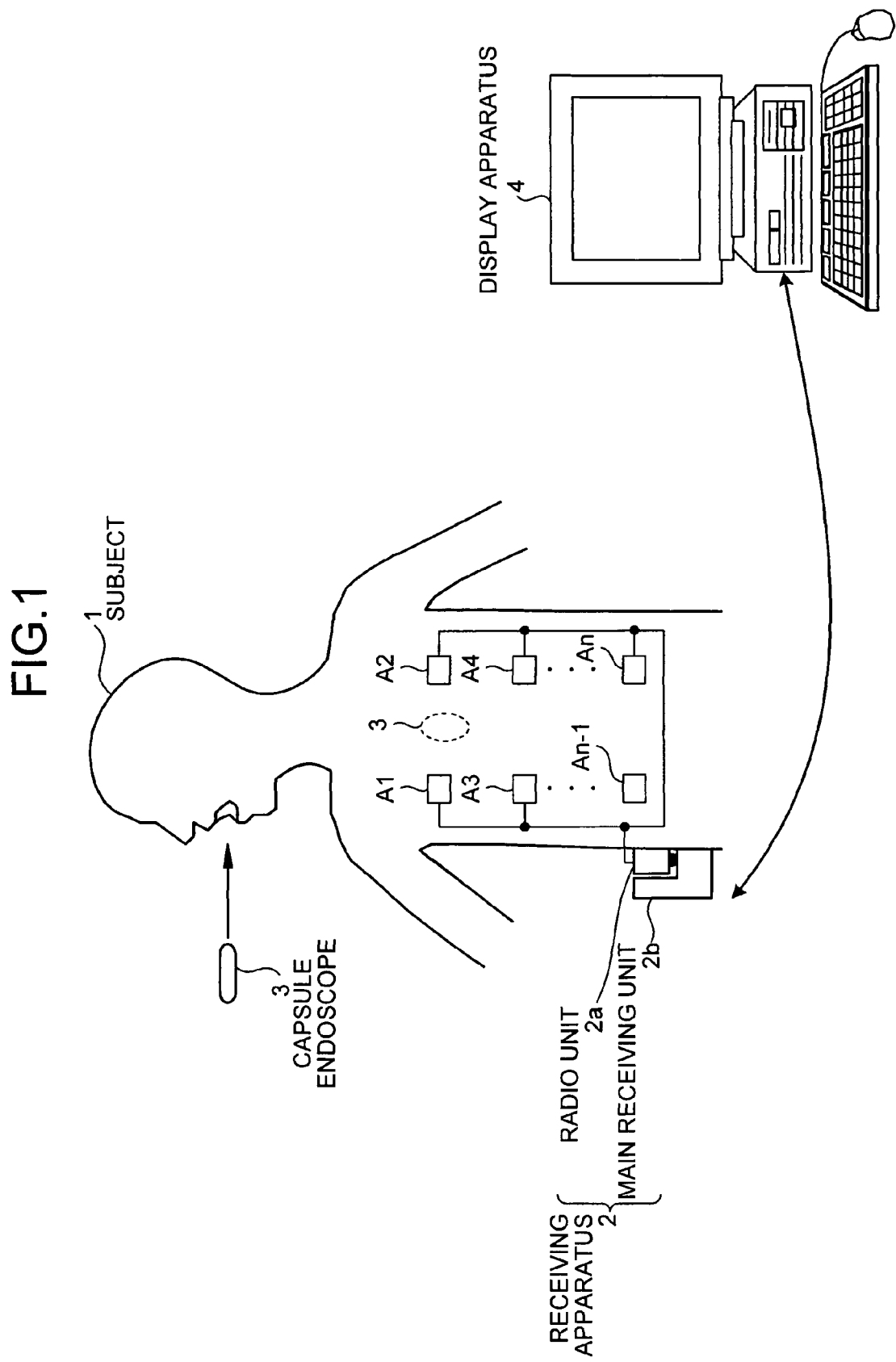
FIG. 1 is a system conceptual diagram illustrating how an in-vivo information acquiring system according to the present invention is configured.

FIG. 1 is a schematic diagram of an overall configuration of a radio in-vivo information acquiring system according to the present invention. The in-vivo information acquiring system uses pantoscopic capsule endoscope as one example of the in-vivo image acquiring apparatus. In FIG. 1, the radio in-vivo information acquiring system includes: a capsule endoscope 3 which is introduced into a body cavity of a subject 1, and picks up body-cavity images so as to transmit data such as an image signal to the receiving apparatus 2 by radio; and a receiving apparatus 2 which is arranged outside the subject 1 and receives body-cavity image data as the image signal radio-transmitted from the capsule endoscope 3. The in-vivo information acquiring system further includes a display apparatus 4 that displays the body-cavity images based on the image signal received by the receiving apparatus 2, and the data are transmitted and received between the receiving apparatus 2 and the display apparatus 4 by wired connection or wireless connection between the receiving apparatus 2 and the display apparatus 4.

The receiving apparatus 2 includes a radio unit 2a having a plurality of receiving antennas A1 to An attached onto an external surface of the body of the subject 1, and a main receiving unit 2b that performs processing on radio signals received via the receiving antennas A1 to An. The units 2a and 2b are connected detachably via a connector or the like. Each of the receiving antennas A1 to An is attached to a jacket which the subject 1 can wear, and the receiving antennas A1 to An may be attached to the subject 1 when the subject wears the jacket. The receiving antennas A1 to An may be detachable from the jacket.

The display apparatus 4 is for displaying body-cavity images picked up by the capsule endoscope 3, and has a configuration like a workstation that displays images based on the data acquired by the receiving apparatus 2. Specifically, the display apparatus 4 may directly display images on a CRT display, a liquid crystal display, or the like, or may output images to another medium such as a printer.

Figure 2:
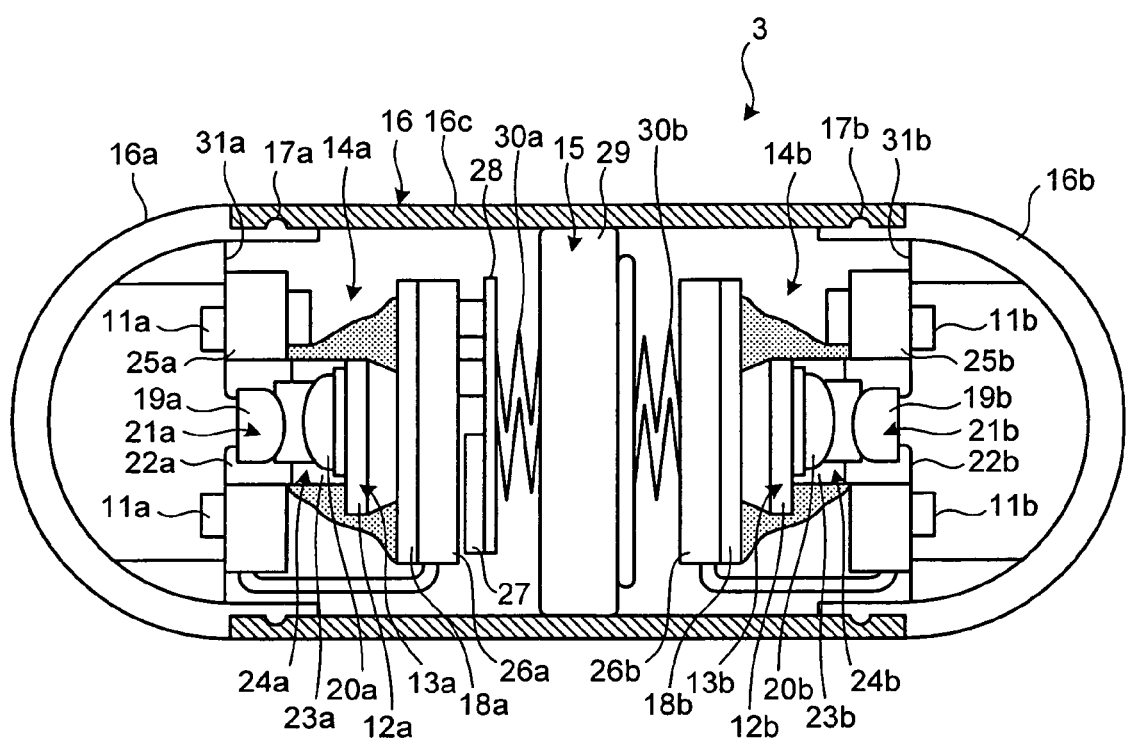
FIG. 2 is a sectional view of an internal configuration of a capsule endoscope.

The capsule endoscope 3 is explained with reference to FIG. 2. FIG. 2 is a sectional view of an internal configuration of the capsule endoscope 3. The capsule endoscope 3 includes two imaging blocks 14a and 14b that have an illuminating unit, such as LEDs 11a and 11b, as first and second illuminating units that illuminates an interior of the body cavity of the subject 1, and imaging units 13a and 13b that has an imaging element, such as CCDs 12a and 12b, as first and second imagers that pick up images in the body cavity, respectively, as a pair, and a power supply unit 15 that supplies power to the above elements, and the imaging blocks 14a and 14b, and the power supply unit 15 are arranged inside a capsule casing 16.

The capsule casing 16 includes transparent end cover casings 16a and 16b of a hemispheric dome shape which cover the imaging blocks 14a and 14b, respectively, and a cylindrical body casing 16c which is engaged with the end cover casings 16a and 16b in a watertight manner via convexo-concave engagement units 17a and 17b, respectively, and in which the imaging blocks 14a and 14b are arranged with the power supply unit 15 placed therebetween. The capsule casing 16 is formed into a size swallowable by the subject 1 from the mouth. The body casing 16c is formed by a color material through which visible light is not transmitted.

The imaging units 13a and 13b include CCDs 12a and 12b which are placed on imaging substrates 18a and 18b, respectively, to image ranges illuminated by the illumination light from the LEDs 11a and 11b (imaging visual field ranges), respectively, and imaging lenses 21a and 21b including fixed lenses 19a and 19b and movable lenses 20a and 20b that form subject images on the CCDs 12a and 12b, respectively. The fixed lenses 19a and 19b are fixed to fixing frames 22a and 22b, respectively, and the movable lenses 20a and 20b are fixed to movable frames 23a and 23b, respectively, thereby forming focus adjusting units 24a and 24b.

The LEDs 11a and 11b are placed on illuminating substrates 25a and 25b, respectively, and are arranged on four places near the left, right, top, and bottom sides of a center of a light axis of the imaging lenses 21a and 21b. Further, in the imaging blocks 14a and 14b, control units 26a and 26b that control the respective units in each block are placed on rear surface sides of the imaging substrates 18a and 18b, respectively, and on one control unit 26a of the imaging block 14a, a wireless substrate 28 is arranged. On the wireless substrate 28, a wireless unit 27 including an antenna for radio communication with the outside is mounted. The imaging substrates 18a and 18b and the illuminating substrates 25a and 25b are electrically connected by cables, respectively, suitably.

The power supply unit 15 positioned between the imaging blocks 14a and 14b includes a button type battery 29 having a diameter approximately matching an inner diameter of the body casing 16c. As the battery 29, a silver oxide battery, a rechargeable battery, a power generating battery or the like may be used. At central portions between the imaging blocks 14a and 14b and the battery 29, spring members 30a and 30b having a torsion-coil-spring-like shape are arranged, respectively, as elastic members which bias the imaging blocks 14a and 14b to the opposing end cover casings 16a and 16b, respectively, i.e., toward the outside. The wireless unit 27 on the wireless substrate 28 and the control unit 26b are electrically connected suitably by a cable or the like which passes through the outside of the battery 29. The wireless unit 27 may not be shared by the imaging blocks 14a and 14b, and it may be individually provided for each of the imaging blocks 14a and 14b.

Locating units 31a and 31b, which come into contact with portions of the outer periphery sides of the illuminating substrates 25a and 25b so as to locate the imaging blocks 14a and 14b in an axial direction of the capsule endoscope 3, are formed integrally near outer peripheries of the insides of the end cover casings 16a and 16b. A rotation preventive locating unit (not shown), which includes a combination of convex and concave portions to be engaged/disengaged with/from each other and locates the imaging blocks 14a and 14b in a circumferential direction around the axis, is formed between the locating units 31a and 31b and the illuminating substrates 25a and 25b.

Figure 3:
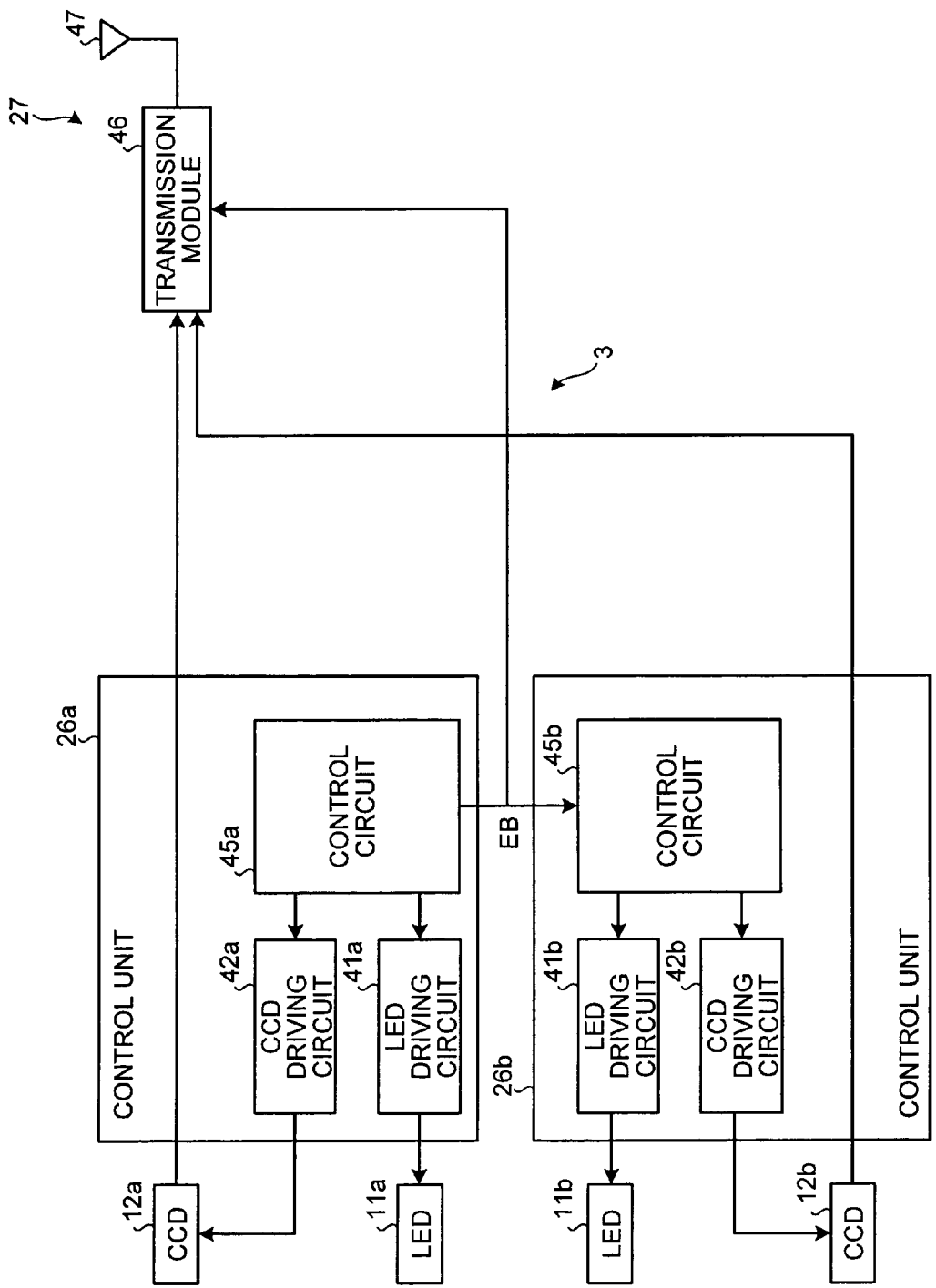
FIG. 3 is a schematic block diagram of an internal circuit configuration of the capsule endoscope.

An internal circuit configuration of the capsule endoscope 3 is explained below with reference to FIG. 3. FIG. 3 is a schematic block diagram illustrating the internal circuit configuration of the capsule endoscope 3. In FIG. 3, the control unit 26a includes an LED driving circuit 41a and a CCD driving circuit 42a corresponding to the LED 11a and CCD 12a, respectively, and controls the paired LED 11a and CCD 12a that are arranged in the front side (i.e., the left side in FIG. 2) of the capsule endoscope 3, for example. Further, the control unit 26a has a control circuit 45a which has a timing generator and a synch generator (not shown) for generating various timing signals and synchronous signals. The control circuit 45a controls the operations and the operation timing of the driving circuits 41a and 42a based on the timing signals and the synchronous signals generated by the timing generator and the synch generator.

The control unit 26b has an LED driving circuit 41b and a CCD driving circuit 42b corresponding to the LED 11b and CCD 12b, respectively, and controls the paired LED 11b and CCD 12b that are arranged in the rear side (i.e., the right side in FIG. 2) of the capsule endoscope 3, for example. The control unit 26b has a control circuit 45b which has a timing generator and a synch generator (not shown) for generating various timing signals and synch signals. The control circuit 45b controls the operations and the operation timing of the driving circuits 41b and 42b based on the timing signals and the synch signals generated by the timing generator and the synch generator.

The control circuits 45a and 45b are in a master-slave relationship such that the control circuit 45a is a master and the control circuit 45b is a slave. The control circuit 45b is driven by the control circuit 45a and performs a control operation according to an enable signal EB from the control circuit 45a. For example, the control circuit 45b operates only while the enable signal EB is at a high level.

The wireless unit 27 includes, as a transmitter provided on an output path of image data picked up by the CCDs 12a and 12b and outputting RF modulated signals, a transmission module 46 and a transmitting antenna 47.

Figure 4:
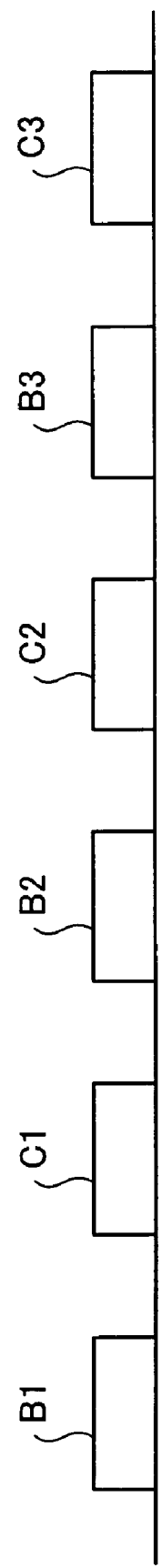
FIG. 4 is a schematic timing chart of one example of output timing of image data controlled by a control circuit shown in FIG. 3.

FIG. 4 is a schematic timing chart of output timing of the image data controlled by the control circuits 45a and 45b. In FIG. 4, B1, B2, and B3 designate image data output from CCD 12a on the front side in frame unit, and C1, C2, and C3 designate image data output from the CCD 12b on the rear side in frame unit. The control circuits 45a and 45b sequentially drive the CCDs 12a and 12b, respectively, in an alternate manner, and control the timing so that illumination timing of the LEDs 11a and 11b is different from output timing of the CCDs 12a and 12b, respectively. That is to say, the LED 11a paired with the CCD 12a is turned on for predetermined time, and after the output operation of the image data from the CCD 12a on the front side is completed, the LED 11b paired with the CCD 12b is turned on for predetermined time so that the output operation of the image data from the CCD 12b on the rear side is performed. Thereafter, such operation control is repeated.

More specifically, the control circuit 45a turns the LED 11a on for predetermined time via the LED driving circuit 41a according to the timing signals output from the generators, and allows the CCD 12a to image the illuminated portion. The control circuit 45a allows the image data B1, B2, and B3 to be output from the CCD 12a to the transmission module 46 via the CCD driving circuit 42a at the timing the LED 11a is turned off. When the output operation is completed, the control circuit 45a outputs the enable signal EB (high level) to the control circuit 45b and the transmission module 46, and switches the control into the control by the control circuit 45b.

The control circuit 45b performs the control operation according to the input of the enable signal EB (high level), and turns the LED 11b on for predetermined time via the LED driving circuit 41b according to the timing signals output from the generators, and allows the CCD 12b to image the illuminated portion. The control circuit 45b allows the image data C1, C2, and C3 of frame unit to be output from the CCD 12b to the transmission module 46 via the CCD driving circuit 42b at the timing the LED 11b is turned off. The control circuit 45a turns the enable signal EB into a low level at the timing the output operation is completed, and switches the control into the control by the control circuit 45a. Thereafter, the above operation control is repeated. Alternatively, in this circuit configuration, the control circuit 45a may turn the enable signal EB into a low level in response to an input of an end signal supplied from the control circuit 45b to the control circuit 45a at the end of output.

Through the above operation, the CCDs 12a and 12b alternately and sequentially output and supply the image data B1, C1, B2, C2, B3, and C3 of frame unit to the transmission module 46, and the image data B1, C1, B2, C2, B3, and C3 are employed as transmission output as RF data. The transmission module 46 has also a function as a transmission data generator of the present invention. The transmission module 46 generates transmission data by adding identification data, which allows identification of the CCD that picks up image data, to each piece of the image data supplied from the CCDs 12a and 12b according to the level of the enable signal EB supplied from the control circuit 45a, and radio-transmits RF data (radio data) based on the transmission data. In the first embodiment, the image data acquired by the CCD 12a and the image data acquired by the CCD 12b are independent. Alternatively, the identification data may be added only to the image data acquired by the CCD 12a, and "zero" (no) identification data may be added to the image data acquired by the CCD 12b. Still alternatively, actual identification data may be added to each piece of the image data.

Specifically, the transmission module 46 determines the image data B1, B2, and B3 input after the input of the enable signal EB of the low level as the image data on the front side picked up by the CCD 12a, and adds identification data representing that the data are picked up by the CCD 12a, e.g., identification data "01" to the image data B1, B2, and B3, and transmits the resulting data. Further, the transmission module 46 determines the image data C1, C2, and C3 input after the input of the enable signal EB of the high level as the image data on the rear side picked up by the CCD 12b, and adds identification data representing that the data are picked up by the CCD 12b, e.g., identification data "10" to the image data C1, C2, and C3, and transmits the resulting data. In the frame, the identification data are added to a former tier of the respective image data, and data of white balance coefficient for executing the white balance adjustment, data for the color processing and the like are added to the image data of each CCD. The image data B1, C1, B2, C2, B3, and C3 shown in FIG. 4 to which various data including the identification data are added are transmitted from the transmission module 46 at frame unit and at predetermined intervals.

Figure 5:
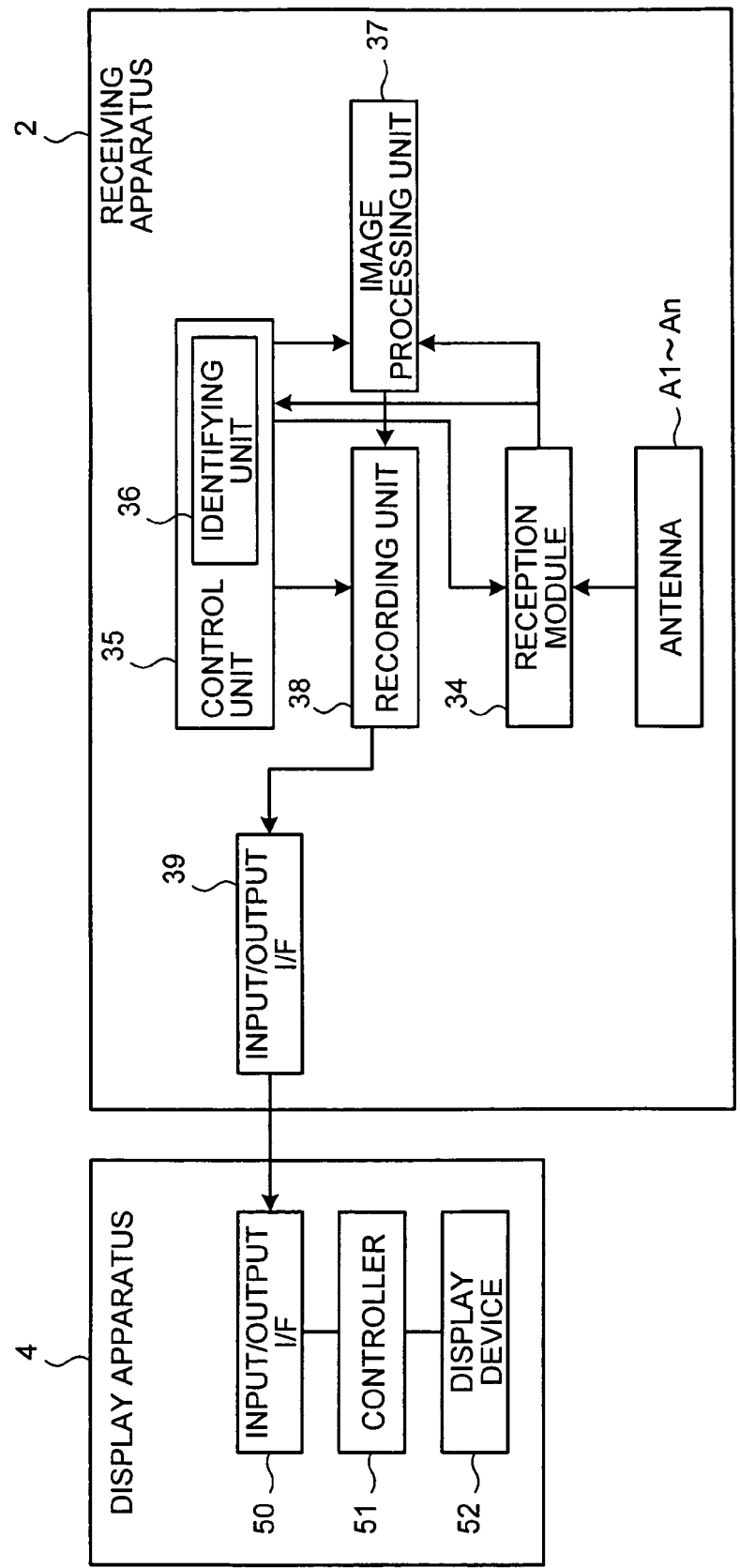
FIG. 5 is a schematic block diagram of internal circuit configurations of a receiving apparatus and a display apparatus.

Internal circuit configurations of the receiving apparatus 2 and the display apparatus 4 are explained below. FIG. 5 is a schematic block diagram of the internal circuit configurations of the receiving apparatus 2 and the display apparatus 4. The circuit configurations of the radio unit 2a and the main receiving unit 2b according to the first embodiment are shown as one block in FIG. 5. The receiving apparatus 2 has a reception module 34, and antennas A1 to An, as a receiver. The reception module 34 has a function of amplifying and modulating electric wave signals captured by the antennas A1 to An, and is configured as the radio unit 2a.

The receiving apparatus 2 has a control unit 35 having an identifying unit 36 as an identifying unit, an image processing unit 37 having a function as a compressor, a recording unit 38 which functions as a storage unit and has separate storage areas for each of the CCDs 12a and 12b, and an input/output interface (input/output I/F) 39 having a function as an output unit. These components constitute the main receiving unit 2b.

The reception module 34 receives the image data transmitted from the capsule endoscope 3 in a frame format via the antennas A1 to An, outputs the identification data of the received frame to the identifying unit 36, and outputs the image data to the image processing unit 37.

The control unit 35 controls the operations and the operation timing of each component, and supplies electric power to each component. The identifying unit 36 determines whether the identification data input from the reception module 34 is the data representing the CCD 12a or the data representing the CCD 12b, and notifies the control unit 35 and the image processing unit 37 of the determined result. Specifically, when the input identification data is "01", the identifying unit 36 determines that the identification data is data representing the CCD 12a, and when the input identification data is "10", the identifying unit 36 determines that the identification data is data representing the CCD 12b, and notifies the control unit 35 and the image processing unit 37 of the determined results.

When the determined result in the identifying unit 36 indicates the CCD 12a, the image processing unit 37 determines that the received image data is image data picked up by the CCD 12a, and executes the white balance adjusting process and the color adjusting process on the image data based on the data on the white balance coefficient and the color process added to the image data. Further, the image processing unit 37 performs moving-image compression on the image data, and after raising the compression rate, stores the image data in the storage area for the image data of the CCD 12a in the recording unit 38.

When the determined result in the identifying unit 36 indicates the CCD 12b, the image processing unit 37 determines that the received image data is the image data picked up by the CCD 12b, and executes the white balance adjusting process and the color adjusting process on the image data based on the data on the white balance coefficient and the color process added to the image data. The image processing unit 37 performs the moving-image compression on the image data, and after raising the compression rate, stores the image data in the storage area for the image data of the CCD 12b in the recording unit 38.

The recording unit 38 is realized by a hard disc device, for example, and retains various images or the like. For example, the recording unit 38 has two divided storage areas. The image data picked up by the CCD 12a and the image data picked up by the CCD 12b of the capsule endoscope 3 are stored in the separate storage areas, respectively. Frame numbers and time are added to the image data according to the receiving order of the image data in the receiving apparatus 2.

The control unit 35 controls the operations and the operation timing of the respective components of the receiving apparatus 2. The control unit 35 controls reading of the image data stored in the storage areas of the recording unit 38, and reads the image data of the CCDs 12a and 12b stored in the storage areas.

The input/output interface 39 is, for example, a USB, which is a serial interface for a personal computer, and outputs the image data of each of the CCDs 12a and 12b read from the recording unit 38 to the display apparatus 4.

The display apparatus 4 has an input/output interface (input/output I/F) 50 having a function as a capturing unit, a controller 51 having a function as a display controller for controlling display, and a display device 52 that displays the image data. The display apparatus 4 has a configuration like a work station or the like such that the controller 51 displays an image on the display device 52 based on data captured by the input/output interface 50. Specifically, the display apparatus 4 may be configured so as to directly display an image on a CRT display, a liquid crystal display, or the like, or to output an image to another medium such as a printer.

Figure 6:
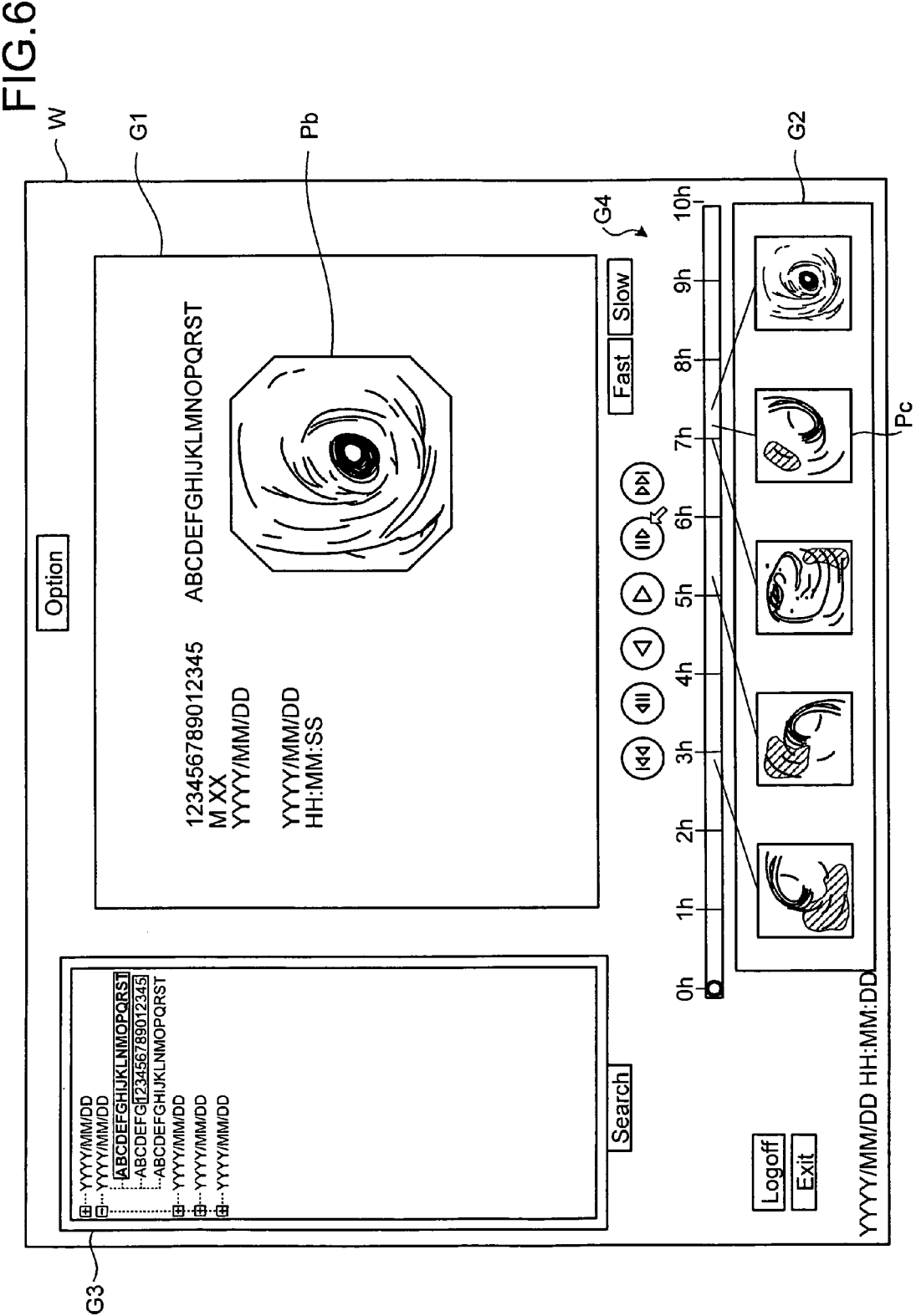
FIG. 6 is a diagram of one example of a display screen of the display apparatus shown in FIG. 5.

The display device 52 displays an image display area (window) W on a display screen as shown in one example of the display screen of FIG. 6. The window W is provided with a body-cavity image display area G1 on which a body-cavity image is displayed, a thumbnail image display area G2 on which a thumbnail image Pc is displayed, an identification information display area G3 on which identification information such as an examination ID or a patient ID is displayed, and a time bar G4. The thumbnail image display area G2 is provided in an area below the body-cavity image display area G1, the identification information display area G3 is provided to a left side of the body-cavity image display area G1, and the time bar G4 is provided in an area between the body-cavity image display area G1 and the thumbnail image display area G2. Further, a group of buttons for moving-image display control, such as a PLAY button, is provided in an area between the body-cavity image display area G1 and the time bar G4.

The controller 51 sequentially displays an image Pb based on the image data captured by the input/output interface 50 on the body-cavity image display area G1 at a desired reproduction frame rate (display rate for reproducing an image). When the image is displayed, the controller 51 controls the display so that the images from the CCD 12a captured previously by the input/output interface 50 are sequentially displayed, and then controls the display so that the images from the CCD 12b captured later are sequentially displayed. As a result, the images from the CCD 12a and the images from the CCD 12b are sequentially displayed on the body-cavity image display area G1 in time division. As to the order in which the image data are captured by the input/output interface 50, the images from the CCD 12b may be captured firstly or the images from the CC 12a may be captured later. As to the display order, the images from the CCD 12b may be displayed firstly.

In the first embodiment, first and second imagers (plural CCDs) acquire the image data of the inside of a subject, and the transmission data generator (transmission module) generates the transmission data by adding the identification data for identifying the CCDs to the image data so as to transmit the transmission data to the receiving apparatus outside the subject. When the image data, to which the identification data for identifying the CCD which has performed the imaging are added, are transmitted and the receiving apparatus outside the subject receives the image data, the identifying unit determines which CCD has picked up the image data based on the added identification data. Therefore, the receiving side can easily recognize which CCD has picked up the image data.

In the first embodiment, the image data are stored separately in the storage areas of the recording unit according to the CCD that is identified by the identifying unit, and the image data of each CCD stored in these storage areas are output to the display apparatus so as to be displayed in time division. Therefore, the image data can be displayed as a series of continuous images on the display apparatus, and a doctor can easily recognize the image.

In the first embodiment, the function of an adding unit is provided to the transmission module 46, but the present invention is not limited to this, and the function of the adding unit may be provided to the control units 26a and 26b, for example. In the first embodiment, the imaging blocks 14a and 14b pick up images at the front and rear sides of the advancing direction of the capsule endoscope 3, but the present invention is not limited to this, and the imaging blocks 14a and 14b may be disposed in the capsule endoscope 3 so as to pick up the images on the right and left sides of the advancing direction, for example, or the imaging blocks may be disposed in the capsule endoscope 3 so that the direction of the light axis (imaging direction) of the imaging blocks 14a and 14b is not parallel but diagonal with respect to the axis of the capsule endoscope 3.

Second Embodiment

Figure 7:
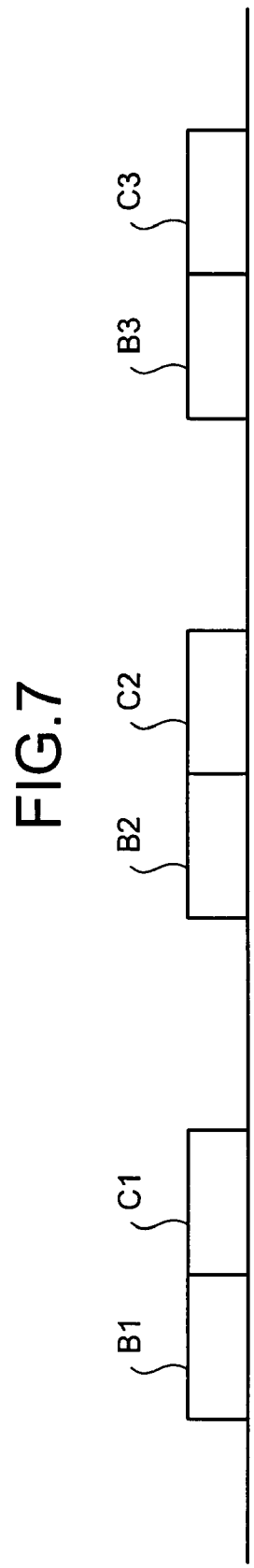
FIG. 7 is a schematic timing chart of one example of transmission timing of the image data.

In the first embodiment, the image data picked up by the CCDs 12a and 12b are individually transmitted to the receiving apparatus, but the present invention is not limited to this, and as shown in FIG. 7, for example, the image data in the front and the rear directions of the capsule endoscope 3 picked up by the CCDs 12a and 12b can be transmitted as an image data pair. FIG. 7 is a schematic timing chart of one example of the transmission timing of the transmission module 46. In the second embodiment, two pieces of image data are combined as an image data pair having a frame format and transmitted from the transmission module 46. For example, two pieces of image data picked up respectively by the CCDs 12a and 12b at closest imaging times, e.g., the image data B1 and C1, the image data B2 and C2, and the image data B3 and C3 are transmitted as the image data pair. The identification data may be added in front of each of the image data so that each piece of the simultaneously transmitted image data can be identified whether it is picked up by the CCD 12a or the CCD 12b.

The receiving apparatus 2 may store each of the received image data pair B1 and C1, the image data pair B2 and C2, and the image data pair B3 and C3 in the recording unit 38 as a pair, or alternatively, the receiving apparatus 2 may store the image data separately depending on which of the CCDs 12a and 12b picks up the same, similarly to the first embodiment. Still alternatively, the display apparatus 4 may sequentially display images based on the image data pair B1 and C1, the image data pair B2 and C2, and the image data pair B3 and C3 so that the images corresponding to two pieces of image data included in each image data pair is displayed simultaneously, or alternatively, the display apparatus 4 may sequentially display images in time division, similarly to the first embodiment.

In the second embodiment, the two pieces of image data which are picked up by different CCDs at closest imaging times are combined as an image data pair and transmitted in one frame. Therefore, intermission between the frame transmission decreases and the time required for transmitting the entire image data can be reduced, in comparison with the first embodiment in which each piece of image data is transmitted as a separate frame.

Further, in the second embodiment, the recording and the display of the received image data can be performed based on the image data pair or based on each piece of the image data, whereby general versatility of the apparatus and the system can be enhanced with respect to the image recording and the image observation.

Third Embodiment

Figure 8:
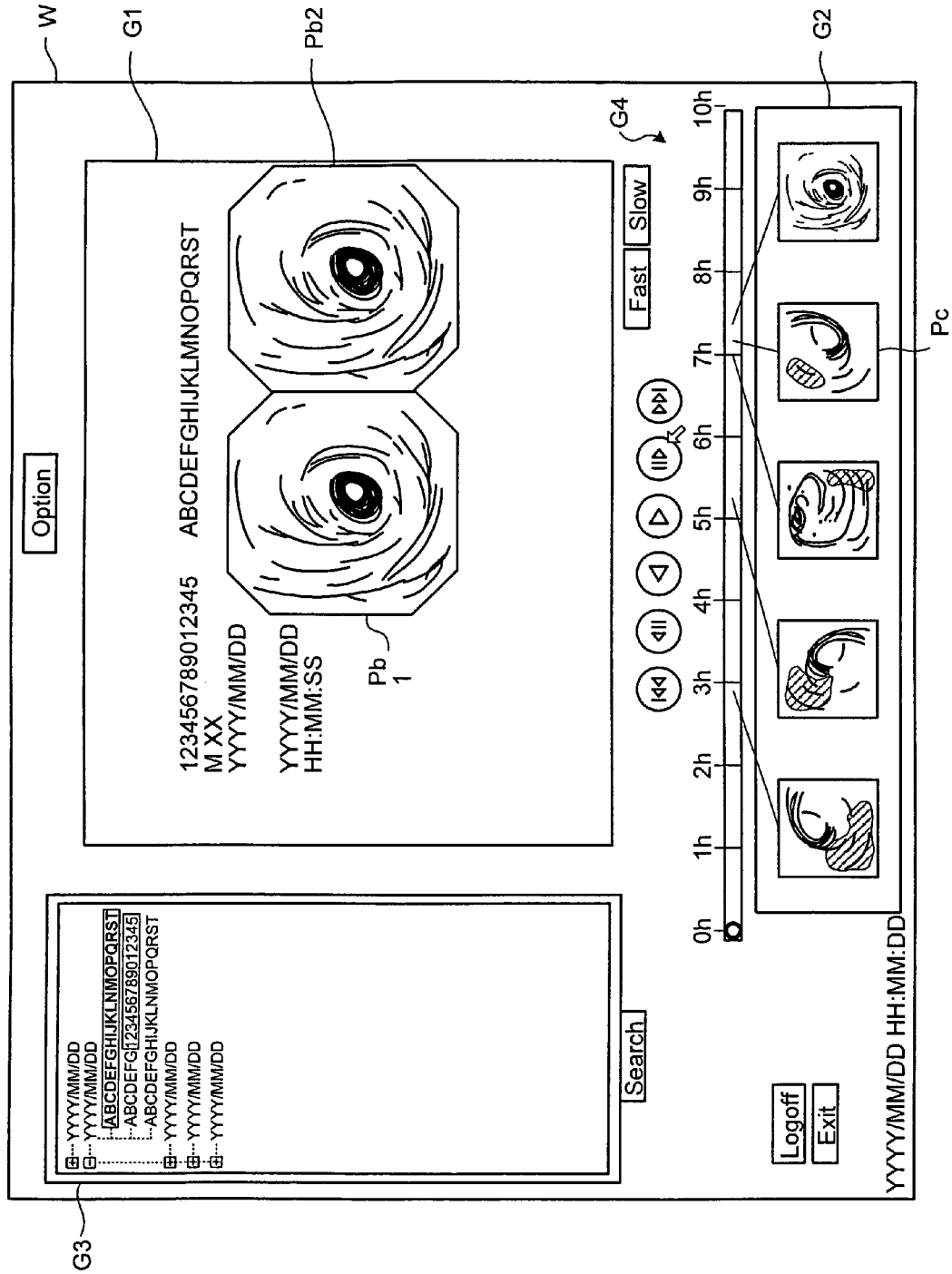
FIG. 8 is a diagram of another example of the display screen of the display apparatus shown in FIG. 5.

FIG. 8 is a diagram of another example of the display screen of the display device 52 shown in FIG. 5. A difference of the display device according to the third embodiment from the display device 52 in the first embodiment is that an image Pb1 picked up by the CCD 12a and an image Pb2 picked up by the CCD 12b are displayed simultaneously on the body-cavity image display area G1.

In the third embodiment, the receiving time at which the receiving apparatus 2 receives the image data is added to the image data and output, and the display apparatus 4 simultaneously displays the images Pb1 and Pb2 whose receiving times are the closest as a pair of images in the body-cavity image display area G1. Specifically, in the display apparatus 4, the controller 51 analyzes the receiving time and controls the display so that the images Pb1 and Pb2 are displayed simultaneously in the body-cavity image display area G1 based on the image data B1 and C1, the image data B2 and C2, and the image data B3 and C3.

In the third embodiment, since the images picked up by the different CCDs can be simultaneously displayed on the display device, the general versatility of the apparatus and the system with respect to the image observation can be further enhanced. The manner of display according to the third embodiment can be applied to a display where a pair of images is displayed simultaneously as in the second embodiment.

Fourth Embodiment

In a fourth embodiment, the controller 51 of the display apparatus 4 determines whether the image picked up by one of the CCDs 12a and 12b is a front-side image or a rear-side image of the capsule endoscope 3 based on an image captured by the input/output interface 50. The controller 51, having a function as a direction detector, estimates whether the acquired image is a front-side image or a rear-side image of the capsule endoscope 3 based on a motion vector. In the direction estimation based on the motion vector, a conventional template matching is utilized.

Specifically, a master image (template) in a certain frame f(t) is superimposed on an image in a next frame f(t+1), and a portion in the frame f(t+1) whose pixel value is the closest to that in the frame f(t) is detected. As a result, the template is searched from the frame f(t+1) so that a motion vector is obtained. The motion vector is obtained for each continuous image of the CCD 12a or the CCD 12b.

The controller 51 obtains a cumulative total value of the directions of the motion vectors obtained for the respective continuous image, and for example, detects whether the cumulative total value directs outward from the center portion of the entire image or directs the center portion from the outer direction of the entire image. When the cumulative total value directs outward, the continuous image is determined as a group of front-side images of the capsule endoscope 3, and when the cumulative total value directs the center portion, the continuous image is determined as a group of rear-side images of the capsule endoscope 3.

When the controller 51 determines that the respective images Pb2 picked up by the CCD 12b are the rear-side image group of the capsule endoscope 3, as shown in FIG. 9, each of the images Pb2 is divided into four rectangular images Pb21 to Pb24 by dotted diagonal lines. Further, the controller 51 controls the display so that the front-side images Pb1 of the capsule endoscope 3 picked up by the CCD 12a are sequentially displayed on the body-cavity image display area G1, and the images Pb21 to Pb24 obtained by dividing the image Pb2 whose receiving time is the closest to that of the image Pb1 are superimposed on four sides of the image Pb1 so as to be sequentially displayed. As a result, in the display apparatus 4, the front-side images are displayed stereoscopically and appear as if the images flow to the rear direction.

The left, right, top, and bottom directions of the CCDs 12a and 12b are defined by a two-dimensional scanning direction of an imaging surface (for example, the scanning from left to right is repeated in a top-bottom direction), and there can be different combinations of the image in the front direction of the capsule endoscope 3 and the divided images in the rear direction varies depending on the difference in the two-dimensional scanning direction. In the fourth embodiment, it is assumed that the CCD 12a performs the two-dimensional scanning repeatedly from the right to the left in a downward direction while the CCD 12b performs the two-dimensional scanning repeatedly from the left to the right in a downward direction.

In the fourth embodiment, based on the cumulative total value of the motion vector direction obtained for each continuous image, it is determined whether the image is the front-side image or the rear-side image of the capsule endoscope, and the front-side image and the rear-side image are displayed by the display apparatus. Thus, the image data in the front and rear directions from the capsule endoscope (in-vivo image acquiring apparatus) can be displayed recognizably.

In the fourth embodiment, when the front-side image and the rear-side image are displayed, the divided rear-side images are superimposed on the periphery of the front-side image so as to be displayed on the display area of the display apparatus. Therefore, the images picked up by the CCDs can be displayed so as to appear stereoscopically, and thus the in-vivo information acquiring system with enhanced general versatility can be provided.

Further effects and modified examples can be derived easily by a person skilled in the art. The embodiments of the present invention are not limited to the above-explained particular embodiments. The present invention therefore can be variously changed without departing from the idea of the present invention.

The in-vivo image acquiring apparatus, the receiving apparatus, and the in-vivo information acquiring system of the present invention are useful when images of the insides of organs of a subject such as a patient are picked up by an imaging device in a wide range. Particularly, they are suitable for the in-vivo image acquiring apparatus, the receiving apparatus, and the in-vivo information acquiring system, which allow for the identification of an image in a group of intra-organ images picked up by plural imaging devices, based on the imaging device.

What is claimed is:

1. An in-vivo information acquiring system, comprising:
    an in-vivo image acquiring apparatus that includes
        a first imager that serves to acquire image data,
        a second imager that serves to acquire image data which is formed independent of the image data acquired by the first imager,
        a transmission data generator that generates transmission data by receiving the image data from the first and the second imagers and adding identification data, which allows for identification of the imager, to each piece of the image data, and
        a transmitter that performs radio transmission based on the transmission data generated by the transmission data generator; and
    a receiving apparatus that includes
        a receiver that receives data transmitted by the transmitter,
        an identifying unit that identifies which imager picks up image data included in the data received by the receiver based on the identification data added,
        a storage unit that has divided storage areas and stores the image data in the storage areas according to the imagers identified by the identifying unit; and
        a compressor that performs moving-image compression separately on the image data among the image data received by the receiver according to the imager which is identified by the identifying unit as the imager picking up the image data.

2. The in-vivo information acquiring system according to claim 1, wherein the transmitter transmits image data picked up by plural imagers as an image data pair.

3. The in-vivo information acquiring system according to claim 1, wherein
    the receiving apparatus further includes an output unit that sequentially outputs the image data stored in the storage unit for each imagers, and
    the in-vivo information acquiring system further comprises
    an image display apparatus that includes
        a capturing unit which captures the image data sequentially output by the output unit, and
        a display controller that controls display so that the image data captured by the capturing unit is displayed in separate display areas according to the imager.

4. The in-vivo information acquiring system according to claim 3, wherein
    the image display apparatus further includes
        a direction detector that finds a motion vector of each image sequence, and detects in which direction of the in-vivo image acquiring apparatus the image sequentially acquired from the receiving apparatus is picked up inside a body cavity, based on the motion vector.

5. The in-vivo information acquiring system according to claim 1, wherein
    the in-vivo image acquiring apparatus includes
        a capsule casing that is formed with end cover casings engaged respectively with two ends of a body casing, and
        a spring member that is in contact with a battery arranged inside the capsule casing, that is compressed when the body casing and the end cover casings are engaged, and that has a biasing force directed towards the end cover casings.

* * * * *